(12) United States Patent
Lori et al.

(10) Patent No.: US 8,480,643 B2
(45) Date of Patent: Jul. 9, 2013

(54) FILM MATERIAL WITH ANTIMICROBIAL AND/OR ODOR-ABSORBING COATING AND SANITARY ARTICLE

(75) Inventors: Fabrizio Lori, Cerese di Virgilio (IT); Sante Aurelio Della Zassa, Padua (IT)

(73) Assignee: Pansac International S.R.L., Milan (IT)

( * ) Notice: Subject to any disclaimer, the term of this patent is extended or adjusted under 35 U.S.C. 154(b) by 802 days.

(21) Appl. No.: 12/515,191

(22) PCT Filed: Nov. 22, 2007

(86) PCT No.: PCT/IB2007/003588
§ 371 (c)(1),
(2), (4) Date: Jun. 26, 2009

(87) PCT Pub. No.: WO2008/062291
PCT Pub. Date: May 29, 2008

(65) Prior Publication Data
US 2010/0080834 A1    Apr. 1, 2010

(30) Foreign Application Priority Data

Nov. 24, 2006   (IT) .............................. MI2006A2253

(51) Int. Cl.
*A61F 13/15*    (2006.01)
(52) U.S. Cl.
USPC ..................................... 604/385.22; 604/382

(58) Field of Classification Search
USPC ........ 604/382, 383, 385.22, 385.23; 428/195, 428/199, 213, 323, 343
See application file for complete search history.

(56) References Cited

U.S. PATENT DOCUMENTS

| | | | |
|---|---|---|---|
| 6,437,212 B1 | 8/2002 | La Fortune |
| 6,649,805 B1 | 11/2003 | Carlucci |

FOREIGN PATENT DOCUMENTS

| | | |
|---|---|---|
| EP | 0 311 344 A1 | 4/1989 |
| EP | 0 445 563 A1 | 9/1991 |
| EP | 1 099 474 A1 | 5/2001 |
| EP | 1 203 531 A1 | 5/2002 |
| EP | 0 749 295 B1 | 8/2002 |
| EP | 1 385 894 A1 | 11/2003 |
| EP | 1 632 253 A1 | 3/2006 |
| WO | WO 99/32697 A1 | 7/1999 |
| WO | WO 2004/063254 A1 | 7/2004 |

*Primary Examiner* — Melanie Hand
(74) *Attorney, Agent, or Firm* — Sahlom Wertsberger; Saltamar Innovations

(57) ABSTRACT

A film material (1) is disclosed herein, particularly a polyolefin-based film material, coated on one side with a water resoluble resin-containing skin (2), and containing antimicrobial and/or odor-absorbing agents susceptible of being activated by organic liquids and blood liquids, such film material is particularly designed to form a disposable sanitary article (4) comprising a liquid-pervious topsheet (5), a liquid-impervious backsheet (6) and an absorbent layer (7) sandwiched between the topsheet (5) and the backsheet (6).

2 Claims, 2 Drawing Sheets

FILM MATERIAL WITH ANTIMICROBIAL AND/OR ODOR-ABSORBING COATING AND SANITARY ARTICLE

A film material is disclosed herein, preferably a polyolefin-based material, and more preferably a polyethylene-based material, which has an antimicrobial and/or odor-absorbing coating.

A process is also disclosed for making a film material having an antimicrobial and/or odor-absorbing coating.

The term "antimicrobial coating" is intended to mean a bacteriostatic (inhibiting the growth of bacteria), bactericide (killing bacteria) fungistatic (inhibiting the growth of fungi, molds and yeasts) or fungicide (killing fungi, molds and yeasts) coating.

The term "odor-absorbing coating" is intended to mean a coating that can absorb objectionable odor molecules, particularly sulfides, amines, fatty acids and ammonia.

This film material is particularly designed for making personal care articles, such as infant diapers, incontinence pads and sanitary napkins, as well as articles for protecting or covering surfaces such as beds and tables.

Particularly, the film material with such coating may be employed as a backsheet of a personal care article.

In a possible embodiment, the film material with the antimicrobial and/or odor absorbing coating is breathable, i.e. allows the passage of water vapor and air to reduce any problem associated to heat- and perspiration-related skin irritations.

The term "breathable material" is particularly intended to indicate a film having an air permeability, based on ATI-CELCA MC 18-74 and TAPPI T 460 om-88 standards, below 100 min/cc of air and a water vapor permeability, based on ASTM D 6701-01 standards, of at least 500 g $H_2O/(m^2 \times 24\ h)$.

This antimicrobial and/or odor-absorbing coating may be also applied to monolithic films, which are especially used as articles for hospitals and clinics in which there is an actual risk of viral transmission.

For improved fitting of the personal care article, the film material may also be elastic.

The term "elastic material" is intended to indicate, for example, a material that, under a stretching load, has a 30% to 70% loss of elasticity (preferably below 40%) and a residual elasticity below 30% (preferably below 10%).

The film material with the antimicrobial and/or odor-absorbing coating may be a laminate, e.g. it may comprise a layer of spun-bonded, SMS, conjugate or carded type, having a variable basis weight, preferably in a range from 5 g/m² to 50 g/m².

Lamination can occur in any well-known method, preferably by application of a hot-melt adhesive on the nonwoven fabric and by contact thereof with the polyolefin film.

Particularly, the film material with the antimicrobial and/or odor-absorbing coating thereon as described below may be as disclosed in EP 1 226 013 B1, WO2005/051635 and MI 2005 A 001615—by the applicant hereof—incorporated herein by reference.

As mentioned above, the film material with the antimicrobial and/or odor-absorbing coating as described hereinbefore is particularly designed to be used as a "backsheet" of personal care articles, such as infant diapers, incontinence pads and sanitary napkins, as well as surface protecting or covering articles.

Organic liquids (such as urine and sweat) and blood liquids excreted by wearers of personal care articles are an ideal "pabulum" for the proliferation of microbes, mold and fungi that can cause skin inflammations and/or irritations.

Malodorous materials result from the degradation of organic fluids, caused by enzymes excreted by certain species of microorganisms.

Depending on specific organic liquids—menses, sweat or urine—most offensive odors are associated to sulfides, amines, fatty acids and ammonia.

In the case of sweat, malodors are due to saprophyte bacteria residing on the skin surface whose action causes the release of particular fatty acids, such as isovaleric acid.

In the case of menses, malodors are particularly associated to the following amine compounds: 1,4 diaminobutane, 1,5 diaminopentane and methyl mercaptan.

Urine may release ammonia due to a urease-catalyzed decay process.

Besides producing a strong offensive odor, ammonia changes skin pH from slightly acid to alkaline and this may be harmful for the epidermis and the skin tissue, and have a direct irritating effect as well as a microbiological infection favoring action.

Odors caused by organic and blood liquids or possibly resulting from their degradation can cause discomfort and other social relationship problems to wearers.

The enzymes that cause the decay of organic components contained in bodily fluids are produced by a variety of bacteria, such as *Escherichia Coli* strains, which reside as commensal of saprophyte flora in almost all human beings.

The elimination of these bacteria by the addition of antimicrobial agents is a preventive odor-controlling measure.

In order to solve the above problems, processes are used that involve the introduction of active ingredients (such as strong chelating agents) in the absorbent material of personal care articles, which sequester calcium so that it is no longer available to microbes, and cause their growth to be delayed.

Active ingredients are further known which inactivate the enzymes that cause or facilitate degradation of organic fluids.

Many patents are known which variously address the problem of reducing odors and bacterial growth, such as: EP 0445 563; EP 0311 344; WO 2006/053373, EP 1291460, WO 01/60299, US 2003/0114806, U.S. Pat. No. 6,649,805, WO 99/32697; WO 2006/017441, EP 1 358 894, WO 2007/053227, EP 1 775 018 A1, WO 2007/018369, EP 1099474.

Nevertheless, these solutions do not provide satisfactory results.

Certain active ingredients added to the absorbent material, such as certain metal salts, are potent urease inhibitors, but some electrolytes can reduce the Absorbent power of SAPs (Super Absorbent Polymers), and affect their effectiveness.

SAP polyacrylates contain free carboxy groups that can bond ammonia and help to control release thereof, and a wide range of these compounds is known in the art, although some of them have an unpleasant odor and low stability.

Furthermore, the release of antimicrobial and odor-absorbing products from the layers of the absorbent article in direct contact with the skin (the topsheet and the absorbent fluff) can cause pH changes, and consequent skin irritations.

It is also known to add scented capsules, with various scents, to the napkins, for odor covering purposes.

Essential oils are effective until organic fluid degradation is initiated, whereupon pleasant scents combine with the unpleasant odors caused by biodegradation and can no longer prevail thereupon.

EP 0 749 295 discloses the making of personal care articles—comprising an absorbent core disposed between a "topsheet" and a "backsheet"—in which the topsheet may contain zeolite impregnated with heavy metal ions, having both odor-absorbing and antibacterial functions.

Furthermore, the absorbent core of the personal care article (pulp fluff) may contain essences designed to be activated by moisture and to cover odors.

U.S. Pat. No. 6,907,025 B2 discloses a personal care article in which the absorbent core contains microorganism spores that can inhibit proliferation of microorganisms residing in organic fluids discharged by the user.

Nevertheless, these prior art solutions still have certain drawbacks.

The object of this invention is to provide a solution to the drawbacks and limitations of the prior art.

Particularly, one object of the invention is to provide a product that can be easily tolerated by human skin, while having a low cost and high effectiveness.

These objects are fulfilled as defined in the independent claims.

Further advantages may be obtained by the additional characteristics of the dependent claims.

A few possible embodiments of the invention will now be described with reference to the accompanying drawings, in which.

Figure 1:
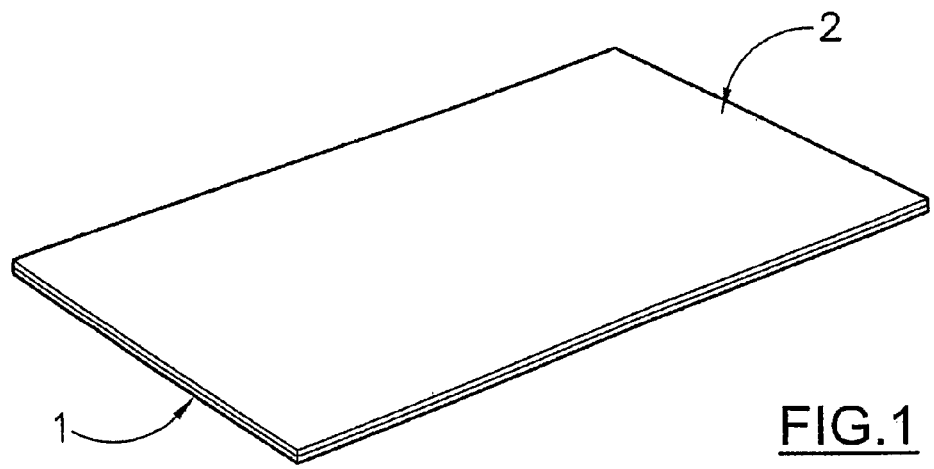
FIG. 1 is a schematic view of a film material coated with a skin containing antimicrobial agents (particularly antibacterial agents) and/or antiodor agents, which is deposited over an entire strip.
Figure 2:
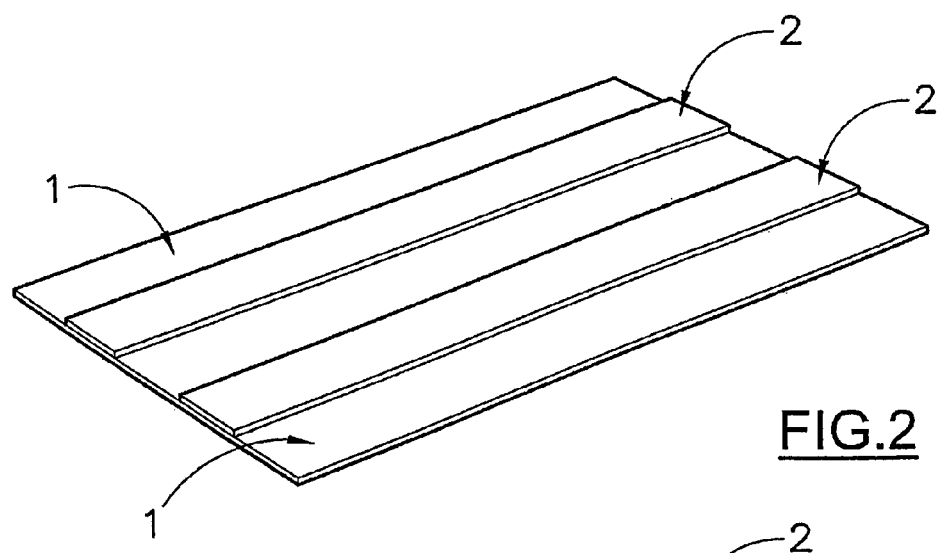
FIG. 2 is a schematic view of a film material covered by continuous parallel strips of a skin containing sanitizing agents (particularly antibacterial agents) and/or antiodor agents.
Figure 3:
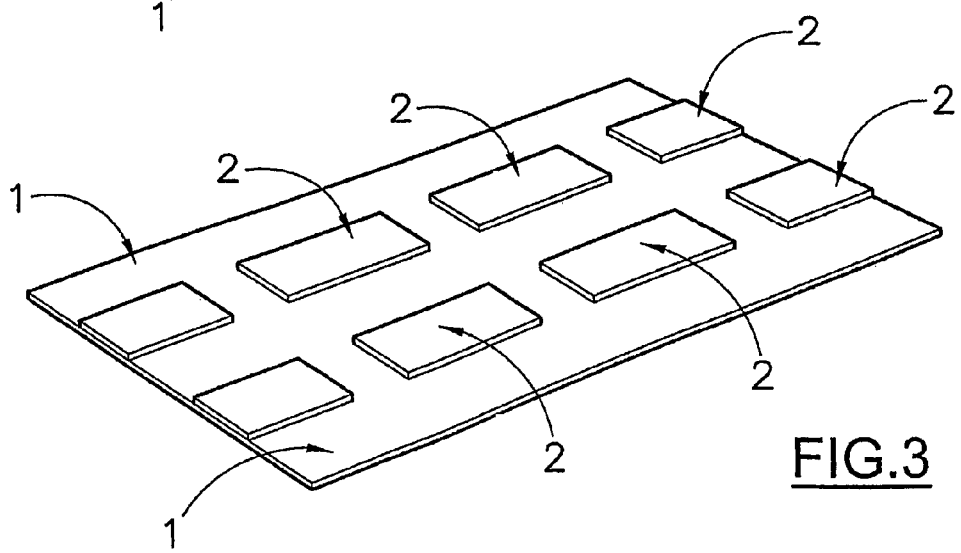
FIG. 3 is a schematic view of a film material covered with discontinuous parallel strips of a skin containing sanitizing agents (particularly antibacterial agents) and/or antiodor agents.
Figure 4:
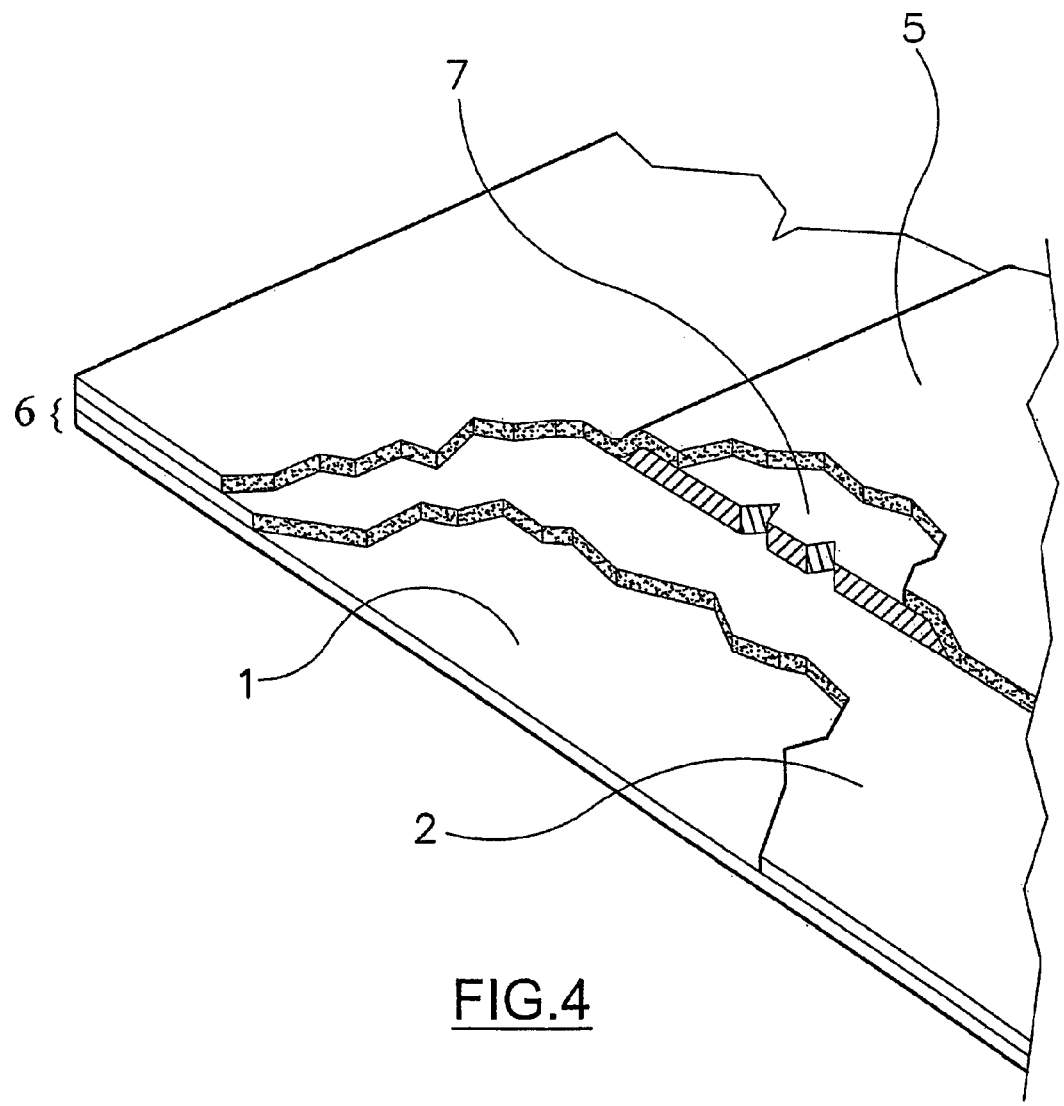
FIG. 4 is a sectional view of a personal care article whose backsheet has a skin on its inner side, that contains antimicrobial (particularly antibacterial) active ingredients and/or odor-absorbing agents.

Referring to the annexed drawings, numeral 1 designates a film material coated on one side with a skin 2 containing antimicrobial and/or odor-absorbing agents, that can be activated by organic liquids and blood liquids.

The film may be entirely covered or have distinct parallel strips extending in the longitudinal, transverse or oblique direction.

Also, the skin 2 may be applied in the form of regularly or randomly arranged areas of various shapes and sizes.

The antimicrobial agents in the skin 2 inhibit the degradation of organic and blood liquids in contact with the skin.

The antimicrobial agents may be of such type as to have an inhibitive effect on the enzymes that favor degradation of organic fluids.

The odor-absorbing agents on the skin 2 absorb the malodorant materials contained in the organic liquids released or produced as a result of organic liquid degradation.

In a possible embodiment, the skin 2 is obtained by printing, such as flexo printing.

Alternatively, the skin 2 may be sprayed.

The film material 1 may be a polyolefin-based, such as a polyethylene-based material.

In a possible embodiment, the film material 1 is breathable but liquid impervious, like the one disclosed in patent EP 1 226 013 B1, by the applicant hereof and currently sold by the applicant under the trade name Mira Air.

The film material 1 may be of the elastic type, like the one disclosed in WO2005/051635 by the applicant hereof and currently sold by the applicant under the trade name Mira Air Elastic.

The film material 1 may also be a laminate, like the one disclosed in MI2005 A 001615 by the applicant hereof and currently sold by the applicant under the trade name Mira Velo.

The film material 1 is mainly designed for making personal care articles, such as infant diapers, incontinence pads and sanitary napkins, as well as surface protecting or covering articles.

The film material 1 may be used for making other articles designed for contact with organic liquids, such as surgical drapes.

Thus, the active ingredients of the antimicrobial and/or odor-absorbing agents in the skin 2 are required to be tolerated by the wearer's skin even upon continued use.

In the making of personal care articles, the film material 1 may be submitted to a number of successive processing steps, such as hot-melt gluing with other materials that form the personal care article.

Thus, the antimicrobial and/or odor-absorbing agents in the skin 2 should be able to remain unchanged up to a temperature of at least 100° C. and preferably of at least 150° C.

Examples of antimicrobial agents contained in the skin 2 include:
  quaternary ammonium salts having alkyl groups from C6 to C30, particularly: lauryl trimethyl ammonium and/or stearyl trimethyl ammonium and/or hexyl trimethyl ammonium and/or benzalkonium chloride,
  biguanides (biguanidine, chlorhexidine),
  mixtures of aluminum oxides, silicon oxides and magnesium oxides,
  chlorhexidine hydrochloride,
  triethyl citrate,
  bioflavonoids, terpenes, terpenoids,
  triclosan,
  silver, zinc, copper salts having an average particle size of less than 1 micron,
  benzoic acid benzoates and esters,
  calcium, sodium, potassium, barium borates.

Powdered silver, zinc, or copper salts have an antibacterial effect against a large number of bacteria and a quick and long-lasting action.

Silver ions can immediately destroy microorganisms, by blocking enzymatic respiration (i.e. energy production), by altering microbial DNA and cell walls.

Odor-absorbing agents contained in the skin 2 include at least one of the following active ingredients:
  zinc ricinoleate,
  zeolites,
  zeolites impregnated with heavy metal ions,
  activated charcoal,
  silica gels,
  flavonoid compounds,
  cyclodextrin ($\alpha$, $\beta$, $\gamma$ cyclodextrins).

The basis weight of the skin 2 may be selected as needed.

In one possible embodiment, the skin 2 may have a basis weight in a range from 0.01 $g/m^2$ to 5 $g/m^2$.

In another embodiment, the basis weight of the skin 2 is in a range from 0.10 $g/m^2$ to 4.5 $g/m^2$.

In one possible embodiment, particularly suited for infant diapers, incontinence pads and sanitary napkins, antimicrobial agents may include a combination of the following active ingredients: bioflavonoids, terpenes, terpenoids, calcium, sodium, potassium and barium borates, and the odor-absorbing agents include zeolites.

Bioflavonoids are intended to include, for example, propolis flavonoids, such as: flavones, flavonols, flavonones.

Bioflavonoids are active both against both gram-negative and gram-positive bacteria (such as *Staphyllococcus aureus*) and against molds and yeasts (such as *Candida Albicans*).

Sodium, potassium and barium borates are bactericide and antifungal products, and particularly barium metaborate inhibits cellulase enzymes, which are used by fungi to destroy cellulose, thereby imparting fungicide ability to the compound.

Benzyl benzoate or other benzoic acid derivatives may be further added as an antibacterial active ingredient.

The skin 2 may be formed from a water suspension adapted to be printed or sprayed on the film material 1.

Antimicrobial and/or odor-absorbing agents are then dispersed in an aqueous solvent and applied to the film substrate in liquid form.

Later evaporation of solvents, obtained by means of hot air, IR lamps or other drying means, provides adhesion of antimicrobial and/or odor-absorbing agents thanks to the action of the suitable non volatile organic binders contained in the aqueous mixture.

The selection of organic binders is based on the requirement that they release the antibacterial and/or odor-absorbing agents as soon as they are reached by any liquid.

Preferably, the skin 2 coats one entire side of the film material 1.

In one possible embodiment, such suspension comprises:
hydroalcoholic solvents,
a plurality of water resoluble resins (acting as binders),
pH stabilizing agents,
surface tension stabilizing agents,
at least one antimicrobial and/or at least one odor-absorbing agent.

The term "hydroalcoholic solvents" is intended to indicate water and alcohol solutions, whose function is to reduce surface tension.

The resins are water resoluble, which means that they use water as a solvent but, after being printed, they dissolve again therein.

In one possible embodiment, hydroalcoholic solvents represent from 40 to 55% by volume and water resoluble resins represent from 30 to 35% by volume.

Alcohol concentration (by volume at ambient temperature) may be of 2% to 7%.

The concentration of pH stabilizing agents is below 1% by volume.

The concentration of surface tension stabilizing agents is below 1% by volume.

Antimicrobial and/or odor-absorbing agents represent from 8% to 15% by volume.

In order to reduce the risk that the skin 2 may be scratched or peeled off during the successive processing steps that are carried out on the film 1, polyethylene waxes may be added to the suspension, up to 3% by volume.

In one possible embodiment, the suspension contains a propolis extract (comprising bioflavonoids, terpenes and terpenoids) calcium, sodium, potassium and barium borates and zeolites.

Propolis may represent from 1% to 30% by volume of the suspension.

The following resins may be used as water resoluble resins:
alkyd resins (synthesis products deriving from condensation of anhydrides, polyalcohols, fatty acids and polyols),
acrylic resins (obtained from the polymerization of acrylic monomers and methyl metacrylate)
epoxy resins (obtained from condensation of epichlorine and bisphenon A)
polyurethane resins (intended as either one-component or two-component resins) are formed of a base (e.g. alkyd resins, polyesters, acrylic resins, etc.) and a curing or catalyst system (aliphatic, aromatic or mixed high molecular weight polyurethane),
vinyl resins (based on chloride and vinyl acetate copolymers).

Other usable resins include nitrocellulose-, silicone-, polyester-resins, styrene-acrylic resins, maleic binders, etc.

These resins may be formulated as solution resins (by salification, generally through amine compounds) or emulsion resins (where water compatibility is imparted by dispersing the polymer in suitable surfactants having a hydrophilic part and a hydrophobic part).

In one possible embodiment, particularly suitable for films designed to make infant diapers, incontinence pads and sanitary napkins, a combination of acrylic resins is used.

The pH of the suspension is preferably of 7 to 9.5.

To protect bioflavonoids in a highly alkaline environment, a buffer was created.

Borates and bioflavonoids (when adequately protected) have a synergistic action in any ratio.

pH stabilizing agents are intended as either inorganic agents, such as ammonium acetate, monoacid and/or salified phosphates, sodium bicarbonate, dihydrogen phosphate-hydrogen phosphate systems, etc, or bio-organic agents such as 4-2-hydroxyethyl-1-piperazinyl ethanesulfonic acid (HEPES), products deriving from aminoacids or protein-proteinate anion systems, or ampholytes.

The agents for controlling the surface tension of the aqueous solution may include silicones and/or mineral oils or other similar materials (low molecular weight silicone surfactants).

In two possible embodiments, the suspension applied to the film is composed as follows (percentages being intended on a volume basis).

|  | First Embodiment | Second Embodiment |
| --- | --- | --- |
| $H_2O$ | 43 (+/−3)% | 50 (+/−3)% |
| Alcohols | 3 (+/−1)% | 3 (+/−1)% |
| Solution containing propolis and calcium, sodium, potassium and barium borates | 20 (+/−2)% |  |
| Additives | <2% | <2% |
| Zeolites | 8 (+/−2)% | 9 (+/−2)% |
| Acrylic resins | 24 (+/−2)% | 35 (+/−2)% |
| Silver salts |  | <2% |

Agents are preferably also provided, such as propylene glycols or the like, which improve suspension and hence improved printability and resolubility of the suspension to be applied.

In one possible embodiment, the suspension is applied at such a speed and using such devices as those of common flexo printing.

Printing may occur at a speed of 40 m/min to 200 m/min.

The skin 2 may be obtained by a process that comprises the steps of:
applying an aqueous suspension as described above on a film material 1 being fed;
drying such aqueous solution applied to the film material 1 to obtain a solid skin 2 adhering to the film material 1.

The aqueous solution is deposited on the film material, for instance, at 2-10 $g/m^2$, either by printing (such as flexo printing) or by spraying.

The active ingredient-containing aqueous suspension may be dried, for instance, by hot air, IR lamps or other means for drying such suspension.

The above material 1 may be used to form a disposable sanitary article 4 comprising:
- a liquid-pervious topsheet 5;
- a liquid-impervious and preferably air- and water vapor-breathable backsheet 1;
- an absorbent layer (fluff) 7, sandwiched between the topsheet 5 and the backsheet 6.

Preferably, the absorbent layer contains SAPs (Super Absorbent Polymers).

It shall be noted that not all organic and blood liquids discharged by the sanitary article wearer are retained by the absorbent layer 7.

It may thus happen that an amount, possibly a little amount, of the organic or blood liquids discharged by the wearer's body can pass through the absorbent layer 7 to reach the backsheet 1.

The organic or blood liquids that reach the backsheet 1 dampen the skin 2 and solubilize the resins of the skin 2 thereby reactivating the antimicrobial and/or odor-absorbing agents contained therein.

This enhances protection of the body parts in direct contact with the backsheet 6 of the sanitary garment, which parts are particularly exposed to skin irritations and/or infections caused by the organic liquids discharged by the wearer.

Furthermore, the antibacterial and/or odor-absorbing agents activated as described above may be also drawn up into the absorbent material 7 (fluff) and pass through the topsheet layer 5 to reach the wearer's skin.

Also, if the backsheet 1 is of the breathable type, it can be exposed to bacterial contamination from the outside.

Indeed, the pores in breathable films have an average diameter of 1 μm, whereas microbes have an average diameter of less than 0.5 μm.

In this case, the antimicrobial skin 2 acts as a sanitary item for complete protection of the wearer against ingress of microbes.

Particular care has been taken by the inventors hereof to product tolerability.

The macromolecular behavior of the compounds used herein obviates the problems of prior art and respects women's privacy and discretion in social life, while providing similar chances to incontinent adults and to children, by operating on the odor threshold and as a protection against bacterial spread.

EXAMPLE 1

Tests were performed, according to the Japanese standard JIS Z 2801:2000, to asses the ability of the antimicrobial skin in personal care products to inhibit proliferation of some common bacteria and fungi, including:

*Escherichia coli*;

*Staphyllococcus aureus*;

*Peseudomonae aeruginosa*;

*Candida albicans*.

The test results are given in the four tables hereinbelow.

Test results relating to *Escherichia coli* within 24 hours in a control inoculum (400 μL), expressed as CFUs (Colony Forming Units)

| Test | Initial value of the inoculum | 2 hours | 24 hours | Percent change after 2 hours | Percent change after 24 hours |
|---|---|---|---|---|---|
| *Escherichia coli* | | | | | |
| Film with no antimicrobial skin | $1.1 \times 10^5$ | $1.2 \times 10^5$ | $2.2 \times 10^5$ | −14.8% | −103.7% |
| Film with a skin containing Ag+ salts | $1.1 \times 10^5$ | $6.9 \times 10^4$ | $3.0 \times 10^3$ | 36.1% | 97.2% |
| Film with a skin containing propolis extract | $1.1 \times 10^5$ | $7.9 \times 10^4$ | $4.1 \times 10^3$ | 22.2% | 96.2% |
| Film with a skin containing Triclosan | $1.1 \times 10^5$ | $5.3 \times 10^4$ | $5.0 \times 10^1$ | 50.9% | 100.0% |

Test results relating to *Staphylococcus aureus* within 24 hours in a control inoculum (400 μL), expressed as CFUs (Colony Forming Units)

| Test | Initial value of the inoculum | 2 hours | 24 hours | Percent change after 2 hours | Percent change after 24 hours |
|---|---|---|---|---|---|
| *Staphyllococcus aureus* | | | | | |
| Film with no antimicrobial skin | $3.8 \times 10^4$ | $1.1 \times 10^5$ | $1.9 \times 10^5$ | −186.2% | −402.7% |
| Film with a skin containing Ag+ salts | $3.8 \times 10^4$ | $1.9 \times 10^4$ | $9.5 \times 10^3$ | 50.8% | 74.7% |
| Film with a skin containing a propolis extract | $3.8 \times 10^4$ | $1.8 \times 10^4$ | $6.7 \times 10^3$ | 53.2% | 82.2% |
| Film with a skin containing Triclosan | $3.8 \times 10^4$ | $1.3 \times 10^4$ | $6.0 \times 10^2$ | 64.9% | 98.4% |

Test results relating to *Pseudomonas aeruginosa* within 24 hours in a control inoculum (400 μL), expressed as CFUs (Colony Forming Units)

| Test | Initial value of the inoculum | 2 hours | 24 hours | Percent change after 2 hours | Percent change after 24 hours |
|---|---|---|---|---|---|
| *Pseudomonas aeruginosa* | | | | | |
| Film with no antimicrobial skin | $9.9 \times 10^4$ | $1.1 \times 10^5$ | $3.3 \times 10^5$ | -9.1% | -3255.2% |
| Film with a skin containing Ag+ salts | $9.9 \times 10^4$ | $9.2 \times 10^4$ | $8.0 \times 10^3$ | 7.0% | 91.9% |
| Film with a skin containing a propolis extract | $9.9 \times 10^4$ | $1.0 \times 10^5$ | $7.2 \times 10^3$ | -1.1% | 92.7% |
| Film with a skin containing Triclosan | $9.9 \times 10^4$ | $8.8 \times 10^4$ | $6.4 \times 10^3$ | 11.1% | 93.5% |

Test results relating to *Candida albicans* within 24 hours in a control inoculum (400 μL), expressed as CFUs (Colony Forming Units)

| Test | Initial value of the inoculum | 2 hours | 24 hours | Percent change after 2 hours | Percent change after 24 hours |
|---|---|---|---|---|---|
| *Candida albicans* | | | | | |
| Film with no antimicrobial skin | $5.1 \times 10^5$ | $5.4 \times 10^5$ | $8.0 \times 10^5$ | -5.9% | -56.9% |
| Film with a skin containing Ag+ salts | $5.1 \times 10^5$ | $6.5 \times 10^4$ | $2.2 \times 10^3$ | 87.3% | 99.6% |
| Film with a skin containing propolis extract | $5.1 \times 10^5$ | $7.0 \times 10^4$ | $2.4 \times 10^3$ | 86.3% | 99.5% |
| Film with a skin containing Triclosan | $5.1 \times 10^5$ | $5.4 \times 10^4$ | $1.9 \times 10^3$ | 89.4% | 99.6% |

EXAMPLE 2

The drawing effect that utilizes the osmotic pressure of fluids was tested according to the Italian standard 002 NMC 93, on two unfolded incontinence pads having a backsheet coated with a skin containing an antimicrobial agent (triethyl citrate and triclosan respectively).

The topsheets (inner side) of the pads were damped with a given amount of water (50 ml) and a square piece (10×10 cm) of absorbent paper was laid on the damped region, and a 4.5 kg weight was laid on the absorbent paper.

The active ingredients migrating to the absorbent paper were extracted using dichloromethane and then determined by gas chromatography.

This analysis was repeated at predetermined time-spaced intervals of 2 to 6 seconds.

This test was used to prove the ability of the active ingredients to migrate through the layers (fluff and topsheet) of the pads and reach the wearer's skin.

The amount of migrating material is expressed as absolute mg of active ingredient extracted by the contacting absorbent paper.

| Triethyl Citrate migration | | Triclosan migration | |
|---|---|---|---|
| Time (seconds) | Absolute mg of Triethyl Citrate | Time (seconds) | Absolute mg of Triclosan |
| 0 | 0.000 | 0 | 0.0000 |
| 2 | 0.026 | 2 | 0.044 |
| 4 | 0.017 | 4 | 0.045 |
| 6 | 0.038 | 6 | 0.16 |

EXAMPLE 3

Two dynamic olfactometry tests were performed on a conventional incontinence pad sample and a pad with a Triclosan- and zeolite-containing skin on its backsheet.

The test was conducted according with the method described in European Standard EN 13725, assimilated in Italy as Standard UNI EN 13725:2004, to determine odor concentration in gas emissions.

Each incontinence pad was prepared by pouring thereon the same amount of urine, i.e. 225 ml, which is deemed to be an average amount produced by an adult human being.

Reduction efficiency is expressed as a percentage, and is determined as the difference between the odor concentration value in the sample containing the incontinence pad with no odor-absorbing agent, and the odor concentration value in the sample containing the incontinence pas with odor-absorbing agents, divided by the odor concentration value in the sample containing the incontinence pad with no odor-absorbing agent, according to the following expression:

$$Eff_{red} (\%) = \frac{C_{od,with.no.abs} - C_{od,with.abs}}{C_{od,with.no.abs}} \cdot 100$$

The table hereinbelow shows that odor concentration in the samples with or without odor-absorbing agents increases with time.

| Time h | $c_{od}$ with no odor abs. agent $ou_E$/mc | $c_{od}$ with odor abs. agent $ou_E$/mc | Efficiency % |
|---|---|---|---|
| 0.5 | 6500 | 2300 | 64.6 |
| 1 | 9700 | 5500 | 43.3 |
| 4 | 21000 | 25000 | -19.0 |

This increase is rather normal because air in the sampling bag tends to saturation with time, thereby attaining an equilibrium between the liquid odor-emitting phase and the gaseous phase, whereupon there can be no further volatilization of odor-emitting materials in the sample and hence no further concentration increase.

More in detail, analysis of the samples with and without odor-absorbing agents respectively, 30 minutes after preparation, showed 64.6% reduction efficiency.

This high value shows the effectiveness of the odor-absorbing film in reducing odor release from the incontinence pad.

EXAMPLE 4

Skin irritation tests were performed on the films containing deposits of propolis solution and Ag+ ions.

The standards that regulate such analyses are ASTM F 719-81 and UNI EN ISO 10993 part 10.

The process consists in applying the sample to be tested on the back of a rabbit, on both sides of the spine, over a suitably dehaired 6 mm² area, and covering it with gauze.

The animals are examined at regular 24 h, 48 h and 72 h intervals, using the following score system:

| ERYTHEMA | score | EDEMA | score |
|---|---|---|---|
| None | 0 | None | 0 |
| Very slight (barely perceptible) | 1 | Very slight (barely perceptible) | 1 |
| Well-defined | 2 | Slight (edges well-defined by definite raising) | 2 |
| Moderate to severe | 3 | Moderate (raised approximately 1 mm) | 3 |
| Severe to slight eschar formation | 4 | Severe (raised more than 1 mm and extending beyond injection area) | 4 |

Then, the Primary Irritation Index is obtained. Irritation classes for the rabbits were determined using the following table:

| IRRITATION CLASS | SCORE |
|---|---|
| Negligible | From 0 to 0.4 |
| Slight | From 0.5 to 1.9 |
| Moderate | From 2 to 4.9 |
| Severe | From 5 to 8 |

The following results were obtained:

| Rabbit | ERYTHEMA | | | EDEMA | | |
|---|---|---|---|---|---|---|
| | 24 h | 48 h | 72 h | 24 h | 48 h | 72 h |
| 33 | 0 | 0 | 0 | 0 | 0 | 0 |
| 34 | 0 | 0 | 0 | 0 | 0 | 0 |
| 35 | 0 | 0 | 0 | 0 | 0 | 0 |

In the above test conditions, the tested materials showed a reaction compatible with a negative control.

EXAMPLE 5

Dynamic olfactometry tests were performed on two sanitary napkin samples, both damped with menstrual discharge, i.e. a conventional one and a sanitary napkin with a skin containing a solution of propolis, borates and zeolites on its backsheet.

The method and instruments used by the Olfactometry laboratory of the University of Milan has been described under Example 3.

The tests have been conducted in as natural and spontaneous conditions as possible, a female volunteer being involved, and 1.45 gr of menstrual discharge were analyzed in both tests. (Value determined as a weight difference between an unused napkin and a used napkin).

The table hereinbelow shows odor concentration values for the two samples with and without the deposit respectively, analyzed at three different time-spaced intervals from sample preparation, i.e. 20, 50 and 165 minutes respectively, as well as the corresponding odor reduction values, as determined with the formula of Example 3.

| Time min | $c_{od}$ with no odor-abs. agent $ou_E$/mc | $c_{od}$ with odor abs. agent $ou_E$/mc | Efficiency % |
|---|---|---|---|
| 20 | 61 | 34 | 44.3 |
| 50 | 64 | 43 | 32.8 |
| 165 | 140 | 81 | 42.1 |

It will be appreciated that odor reduction efficiency values are maintained approximately constant with time, in a range from 33% to 44%.

More in detail, in the first analysis, carried out 20 minutes after sample preparation, 44.3% reduction efficiency was found.

In the second analysis, carried out 50 minutes after sample preparation, 32.8% reduction efficiency was found.

Finally, in the third analysis, carried out 165 minutes after sample preparation, 42.1% reduction efficiency was found.

These high efficiency values show the effectiveness of the odor-absorbing film in reducing odor release from the napkins under test.

The invention claimed is:

1. A disposable personal care article, comprising:
a liquid-pervious topsheet;
a liquid-impervious backsheet;
an absorbent layer, sandwiched between said topsheet and said backsheet;
wherein said backsheet comprises a film material coated with a skin containing water resoluble resin, and water resoluble resin comprises at least one resin selected from a list consisting of:
alkyd resin;
polyurethane resins;
acrylic resins;
epoxy resins;
vinyl resins, and
a combination thereof;
wherein said skin contains antibacterial active ingredient and odor-absorbing active ingredient,
said antibacterial active ingredient comprising an agent selected from a list consisting of bioflavonoids, terpenes, terpenoids, calcium, sodium, potassium, barium borates, and a combination thereof;
said odor-absorbing agent comprising zeolites,
wherein the combination of said antimicrobial active ingredients and odor-absorbing active ingredient is susceptible of being activated by organic liquids,
and wherein said skin facing towards said topsheet and said absorbent layer;
wherein said skin contains polyethylene wax.

2. A disposable personal care article, according to claim 1, wherein said skin has a basic weight in a range from 0.01 to 5 g/m2.

* * * * *